(12) United States Patent
Wellman et al.

(10) Patent No.: US 6,652,518 B2
(45) Date of Patent: Nov. 25, 2003

(54) TRANSMURAL ABLATION TOOL AND METHOD

(75) Inventors: Parris S. Wellman, Hillsborough, NJ (US); Rajesh Pendekanti, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/966,813

(22) Filed: Sep. 28, 2001

(65) Prior Publication Data

US 2003/0069572 A1 Apr. 10, 2003

(51) Int. Cl.$^7$ ............................................. A61B 18/18
(52) U.S. Cl. ......................................... 606/41; 607/101
(58) Field of Search ........................... 606/41, 42, 45, 606/46, 48, 51; 607/101, 115, 116, 122

(56) References Cited

U.S. PATENT DOCUMENTS

| | | | | |
|---|---|---|---|---|
| 5,569,242 A | * | 10/1996 | Lax et al. ...................... | 606/42 |
| 5,697,928 A | | 12/1997 | Walcott et al. ................. | 606/41 |
| 5,904,711 A | | 5/1999 | Flom et al. ................... | 607/129 |
| 6,012,457 A | | 1/2000 | Lesh ........................... | 128/898 |
| 6,030,384 A | * | 2/2000 | Nezhat ........................ | 606/48 |
| 6,068,628 A | * | 5/2000 | Fanton et al. ................ | 606/41 |
| 6,079,414 A | | 6/2000 | Roth ........................... | 128/898 |
| 6,161,543 A | | 12/2000 | Cox et al. .................... | 128/898 |
| 6,164,283 A | | 12/2000 | Lesh ........................... | 128/898 |
| 6,237,605 B1 | * | 5/2001 | Vaska et al. ................. | 128/898 |
| 6,245,064 B1 | | 6/2001 | Lesh et al. .................... | 606/34 |
| 6,251,109 B1 | | 6/2001 | Hassett et al. ................ | 606/45 |
| 6,290,699 B1 | * | 9/2001 | Hall et al. ................... | 606/41 |
| 6,402,746 B1 | * | 6/2002 | Whayne et al. ............... | 606/41 |
| 2002/0058934 A1 | * | 5/2002 | Wang et al. ................... | 606/41 |

OTHER PUBLICATIONS

Javier Roman–Gonzalez et al. "Collateral Tissue Injury Occurring During Intrapericardial Catheter Ablation in the Closed Chest Canine Model" North American Society for Pacing and Clinical Electrophysiology 22$^{nd}$ Annual Scientific Sessions, Hynes Convention Center, Boston, massachusetts, USA 388 (May 2–5, 2001).

David E. Haines et al. "Rapid, Continuous and Transmural Linear Ablation With a Novel Bipolar Radiofrequency Ablation System" North American Society for Pacing and Clinical Electrophysiology 22$^{nd}$ Annual Scientific Sessions, Hynes Convention Center, Boston, Massachusetts, USA 388 (May 2–5, 2001).

* cited by examiner

*Primary Examiner*—Michael Peffley
(74) *Attorney, Agent, or Firm*—Nutter McClennen & Fish LLP

(57) ABSTRACT

An ablation method and device contacts one surface of a target layer and positions the tissue to ablate entirely through the layer. The tissue may be a wall of the heart (ablated, for example, to form blocking lesions for atrial fibrillation), and ablation may be performed with the heart stopped or beating, and effected by either endocardial or epicardial contact. Access may be through an open incision or a minimally invasive technique involving a small opening through which one or more elongated surgical tools are inserted. Illustratively, an atrial ablation treatment can be performed prophylactically (after CABG), or independently to treat an existing condition. A tool of the present invention has a handle at a proximal end, a bipolar ablation head, and an elongated body interconnecting the handle and the ablation head. A channel or contoured surface fixes and bends the tissue such that inter-electrode conduction paths span the thickness of the layer, thus dependably creating a fully transmural ablation lesion. The oriented transmural energy conduction paths reduce the possibility of inducing coagulation of blood in the heart chamber. One bipolar assembly has an electrode spacing of approximately ten millimeters across a channel of about five millimeters depth. Preferably the ablation head forms a suction holder, connected through internal passages to a vacuum pressure of about 100–500 mmHg, and immobilizes the contacted tissue.

22 Claims, 6 Drawing Sheets

TRANSMURAL ABLATION TOOL AND METHOD

CROSS-REFERENCE TO RELATED APPLICATION

Field of the Invention

The present invention relates to tissue ablation and more particularly to methods and devices for creating effective ablation extending entirely through a layer of tissue. It has particular application to methods and devices for ablating foci and for forming conduction blocking lesions in a wall of the heart.

Background of the Invention

Over the last decade, the field of electrophysiology, especially mapping and treatment of arrhythmias of the heart, has grown spectacularly. A great number of ablation tools and catheters have been devised, and procedures have been methodically tested employing a number of catheter-like ablation devices, often with structures specifically constructed to enable the instrument to place a specific lesion at a site or region. Among catheter-based cardiac interventional techniques, the most common employ either high frequency (RF) electrical energy or cryogenic cooling to ablate tissue and cause scarring. Other available catheters employ laser illumination, microwave energy or heated surface contact to ablate tissue at a region or along a path operative to destroy aberrant tissue or disconnect an aberrant conduction pathway. These cardiac treatment methods require mapping of the aberrant foci within the heart, and then selective ablation of foci, or lines that isolate the foci, in the heart wall. Such ablation treatment is generally a time-consuming and complex procedure.

A number of these catheters are configured for percutaneous insertion to their point of application, for example, along a vessel into a chamber of the heart to form an endocardial lesion. Still others, both hand-manipulated and catheter-manipulated devices, may be configured for epicardial application. In addition, a hybrid approach has been developed which involves tools and devices similar to those developed for minimally invasive or endoscopic surgeries; these surgical or treatment devices reach the target tissue thoracoscopically through a small port or opening port passing through the myocardial wall to access the interior of the heart.

Each of these approaches has its own particular advantages and constraints. Thus, for example, basket catheter constructions are intended for delivery (typically along an endovascular route) into a cardiac chamber, and seek to provide an expanded electrode structure that may maintain itself in fixed contact with the endocardial wall of a still-beating heart for protracted time periods, so that mapping and ablation operations may be carried out in a fixed frame of reference at plural discrete points or along discrete arcs or segments. Still other catheters may have ablation tips with a particular geometry effective to provide oriented arc or segment lesions. Many common catheter devices act as drag electrodes with an ablation tip that "draws" lines of conduction block, ablating tissue at its point of contact as the tip is moved along the heart wall, allowing greater flexibility in placement, but at the expense of stability of positioning. Such catheter tips may require (and include) one or more barbs or prongs that penetrate the cardiac wall to anchor the ablation tip assembly.

Typically, the locations of lesions determines their effectiveness against particular re-entrant signal paths, so a preliminary mapping step is usually necessary. The requirement that a physician map sites or conduction patterns and then create a number of separate lesions positioned to destroy those sites or block re-entrant pathways, dictates that a cardiac treatment procedure be relatively lengthy. Often, once a lesion is created in a chamber wall, the chamber must be remapped to assure that block has occurred and that the tissue is not simply stunned. Thus it may be necessary to confirm conduction patterns after waiting a number of minutes, and it may also be necessary to re-ablate a lesion if the initial treatment lesion did not extend deeply enough to be effective, or was inaccurately placed or otherwise ineffective.

One area of particular interest is that of atrial fibrillation. Atrial fibrillation is a commonly occurring disorder characterized by erratic beating of the atrium, a condition that may result in thrombogenesis and stroke. While medication can be effective for some cases, many patients are not responsive to medical therapies, and effective treatment of those resistant cases calls for creating lesions in the atria to form effective conduction block. The Cox surgical MAZE procedure addresses this problem by stopping the patient's heart, opening the atrium and dividing the chamber wall into pieces which are then sewn back together. The result of such surgery is to create scar tissue extending entirely through the cardiac wall and located along the cut lines. The scar tissue effectively blocks electrical conduction across the cut lines, and these divide the atrium into a number of sub-regions that are each too small to support a re-entry pathway. The surgical MAZE technique, however, requires that the heart be stopped, so it suffers from the morbidities associated with placing the patient on cardiopulmonary bypass and stopping the heart. It is also time-consuming and technically difficult to perform.

It has been found that a number of atrial arrhythmias originate at positions within a pulmonary vein and propagate into the atrial wall. Several specialized catheters have been described in the literature to treat these arrhythmias, with a construction that can be inserted through a heart chamber to a pulmonary vein and used to ablate a circumferential blocking lesion in the tissue of the vein or around the pulmonary os. U.S. Pat. No. 6,012,457 shows one such device. However, ablating circumferentially within a pulmonary vein can cause pulmonary vein stenosis. U.S. Pat. No. 6,161,543 also addresses the treatment of atrial fibrillation arising from such venous arhythmia sites, describing an ablation method and tool that percutaneously access the heart and penetrate the cardiac wall with an ablation tool to endocardially contact the atrial wall and form a cryogenic lesion surrounding the pulmonary veins.

Positive results have been reported for such systems. However, it also seems likely that a more complicated lesion set will be required to be fully effective in the majority of patients, and the variable thickness of the cardiac wall at the os may be quite variable, making the formation of a fully transmural blocking lesion problematic.

In addition to cardiac ablation catheters, a number of tools exist for ablating other tissue and performing common surgical tasks, such as coagulating vessels encountered during surgery to prevent bleeding. Many of these tools have a basic shape similar to a scalpel, forceps or other hand tool, with ablation electrodes positioned in a tip or jaw region. RF ablation tools of this sort may be monopolar or bipolar.

Monopolar ablation systems generally have a single electroded surface as the active ablating contact element, and utilize a large area return electrode to complete the current circuit. The return electrode is generally placed on the patient's skin. Effective operation of such systems relies on the fact that current density becomes high, and ablation occurs, only in a small region close to where the active electrode contacts tissue. Bipolar systems, on the other hand, employ two closely spaced electrodes of opposite polarity to define the current paths through tissue. The current is high because the electrodes are near to each other, and both electrodes are of comparable size, so the high current region spans the tissue volume lying between the electrodes. Bipolar electrodes may be expected to form better-defined ablation lesions, since current will not vary unexpectedly as movement of the active electrode results in changing impedance pathways to the return electrode. However, the provision of a high intensity local current path between two electrodes poses the problem of positioning the tool without damaging unintended sites.

In the area of cardiac ablation, these problems are compounded since the cardiac chambers are normally full of blood, which is highly conductive and is prone to coagulation when overheated.

It is therefore desirable to provide ablation devices, systems and methods that dependably form a defined lesion extending entirely through a layer of tissue, such as cardiac tissue.

SUMMARY OF THE INVENTION

The present invention provides a method and a tool implementing the method, for safe and effective ablation of tissue. An ablation head is arranged to engage a surface of the target tissue, and two or more electrodes are arranged in a bipolar electrode configuration thereon to ablate the tissue. The electrodes are positioned with respect to the tissue engaged by the ablation head such that the inter-electrode current paths span the thickness dimension of the tissue layer. The method and device assure that ablation occurs through the full thickness of the tissue layer, while generally preventing the current paths from extending to adjacent volumes at which blood coagulation or unwanted tissue damage could occur.

The invention is quite general in scope. As applied to the heart, the heart may be stopped or beating, and the device may be configured so electrodes make endocardial or epicardial contact. Access to the target tissue may be either through an open incision, or by a minimally invasive technique involving a small opening through which one or more elongated surgical tools or endoscopic devices are inserted. As applied to cardiac tissue, methods and devices may, for example, form blocking lesions effective to prevent atrial fibrillation. Furthermore, a procedure in accordance with the present invention can be performed as either a stand-alone procedure, or may be carried out as a prophylactic procedure performed after a coronary artery bypass graft (CABG) operation to prevent perioperative onset of arrythmia, such as atrial fibrillation.

An ablation tool of the present invention has a handle at a proximal end, an ablation head at a distal end, and an elongated body interconnecting the handle and the ablation head. The ablation head includes a channel or other shape, and preferably also includes a structure or mechanism that grips or otherwise fixes the position of tissue that it contacts. A bipolar arrangement of electrodes defines localized tissue ablation along short paths between electrodes and through tissue secured by the ablation head structure. The channel and/or gripping mechanism immobilizes tissue in a position such that the conduction paths between the opposed electrodes span the thickness dimension of the tissue layer (e.g., the cardiac wall, in this example). The ablation head may grip with a suction force and tissue may be immobilized, for example, by means of suction apertures communicating with a vacuum passage, thus drawing the tissue down toward the apertures and bending the wall to effect a transmural ablation. A tissue-gripping force may alternatively be provided mechanically, by implementing the ablation tool as a pair of forceps or tongs with opposed electrodes formed on the jaws of the tool. Another embodiment has an ablation head having a contact face configured as a channel or as a concave wall, as seen in cross-section across a long axis. Two or more electrodes are positioned on the contact face to define short inter-electrode paths through the channel or concavity such that manually-exerted pressure of the ablation head against tissue forces the tissue into the channel or concavity and bends the tissue into position for through-layer ablation.

The electrodes and other ablation head structure may be rigidly affixed to the end of the elongated body, and may for example be affixed transversely to allow the body to push the contact face against tissue when manipulated by the handle, forming a through-wall ablation along the band of tissue in the channel. Alternatively, the ablation head may extend from the tool body such that drawing the handle along the axis of the body drags the electroded face along a path on the tissue surface, forming a through-wall ablation along a band of tissue in the path.

For treatment of a cardiac arrhythmia due to re-entrant pathways or signals originating in the region of the pulmonary veins or elsewhere, the ablation devices of the present invention allow effective bi-polar formation of lesions by contact with a single surface (endocardial or epicardial) of the cardiac wall while assuring that the legions extend entirely through the wall. The channel positions the tissue such that the primary conduction paths between electrodes of opposite polarity extend directly through the full layer of tissue. The transmural ablation energy paths so defined reduce the possibility of inducing coagulation in any blood present in the cardiac chamber.

Ablation heads for devices of the present invention may have relatively short or small electrodes for forming spot-like or drag-line ablation regions, or may have longer arc- or linear segment-electrodes for forming defined arcuate or segmental lesions. One ablation head is discretely sized to be manipulated between adjacent pulmonary veins for creating relatively small lesions in the cardiac wall, extending through the wall and circumferentially surrounding one or more of the veins, e.g., about one vessel, or about a pair of pulmonary veins. Another ablation head may be sized to function as a drag line ablator for forming lesions along a path, e.g., extending from a circumferential lesion at the pulmonary veins down to the mitral valve.

For use on the cardiac wall, an ablation device preferably has a bipolar head with opposed electrodes spaced approximately ten millimeters apart, across a channel which may have a depth, e.g., of about five millimeters. The channel is effective to allow cardiac wall tissue to enter the channel and position at least one transmural thickness directly in the current pathways between the opposed electrodes while substantially excluding the interior chamber (when applied epicardially) from crossing the current paths. The channel may be formed as a U-shaped channel with bipolar electrodes of opposed polarity on opposite sides thereof to form a single current path or band. Alternatively, the channel may have another shape—rectangular, circular, elliptical or simply a shallow dished concavity. Furthermore, additional electrodes may be provided such that ablation regions are defined by multiple path segments. Thus, for example, an electrode of one polarity may be located in the bottom of the channel and act together with several electrodes of the opposite polarity situated on respective side walls of the channel. Other embodiments have a curved or dished channel with bipolar electrode segments positioned to create a transmural lesion forming path when tissue is held therein. Preferably the channel operates as a vacuum chuck, with suction applied through internal passages maintained at a vacuum pressure of about 100–500 mm Hg to draw tissue into the channel and position it relative to the ablation electrodes. Most preferably, a seal extends along the contact face.

BRIEF DESCRIPTION OF THE DRAWINGS

The invention will be understood from the description herein of illustrative embodiments and comparative examples, taken together with the figures, wherein.

DETAILED DESCRIPTION OF THE INVENTION

By way of overview, an ablation tool of the present invention is configured for RF ablation with bipolar or multipolar electrodes arranged to contact a layer of tissue and ablate entirely through the layer. A contact surface of an ablation head that carries the electrodes is arranged to engage the surface of the target tissue layer, which may, for example, be myocardial tissue such as a wall of the heart, and two or more electrodes are arranged to define effective bipolar ablation current paths to ablate the tissue while it is engaged by the contact surface. The geometry is such that the inter-electrode current paths span the thickness dimension of the tissue layer, while generally assuring that the current paths do not extend to areas where blood coagulation or unwanted tissue damage would occur.

Figure 1A:
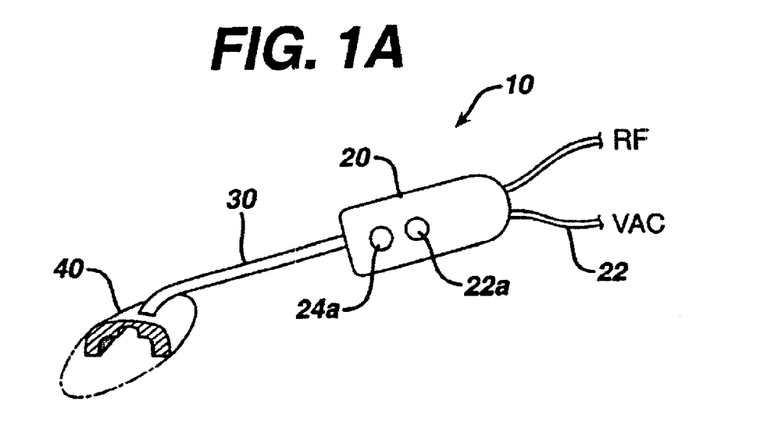
FIG. 1A illustrates a first embodiment of an ablation device in accordance with the present invention in a partially cutaway schematic perspective view.
Figure 1B:
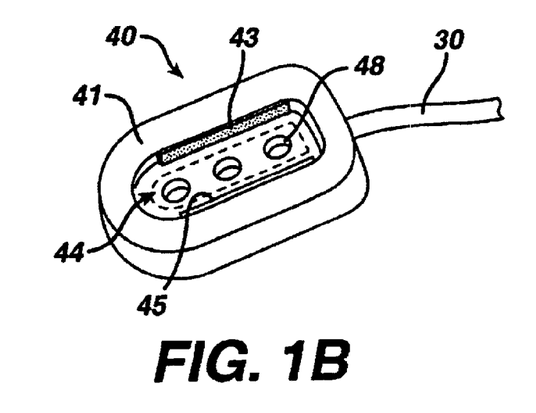
FIG. 1B illustrates the embodiment of FIG. 1A in a bottom perspective view.
Figure 1C:
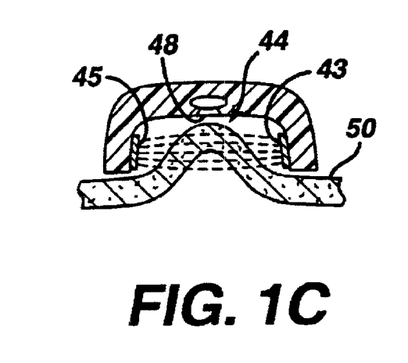
FIG. 1C illustrates the embodiment of FIGS. 1A and 1B in a cross-sectional view.

FIGS. 1A–1C show a first embodiment of an ablation device 10 in accordance with the present invention. As shown in FIG. 1A, device 10 includes a handle 20, an elongated shaft or body 30 and an ablation head 40. The ablation head is a bipolar ablation head, having electrodes that are impressed with signals of different polarity, so that current flows between a pair of electrodes on the head. As shown schematically, the ablation head 40 is elongated, extending along a long dimension, and as partially illustrated in cut-away, the head 40 has a central groove or channel 44, and the electrodes 43, 45 extend along the groove so that tissue in the groove lies in the conduction path between electrodes.

FIG. 1B shows the ablation head of FIG. 1A inverted, with electrodes 43, 45 extending along the channel 44. A plurality of apertures 48 open into the channel, and these communicate, via one or more suction passages extending from the head through body 30 and handle 20, to a source of suction, such as a hospital's vacuum suction wall connector. For this purpose, a suction line-connection 22 and a suction control button 22a are shown (FIG. 1A).

FIG. 1C is an enlarged cross-sectional view of the ablation head 40 in a plane across the channel 44, illustratively showing a layer of tissue 50 held therein by the suction apertures 48 when suction is applied. The apertures 48 communicate with a suction passage 48a in the ablation head, that in turn connects through the body 30 and handle 40 to a source of suction. As further shown, the layer of tissue 50 (such as cardiac wall tissue) curves into the channel, and is thus positioned so that the full thickness dimension of the layer is spanned by the higher current, short, direct paths between opposed electrodes 43, 45 at the sides of the channel. For application to a heart wall having a thickness of about five millimeters, a suitable cavity (channel) depth is about 5 mm with about a 10 mm width at the cardiac surface. The cavity does not need to be rectangular but can be any closed shape, e.g. a circle, an ellipse, or a rectangle with rounded corners. Furthermore, while FIGS. 1A and 1B illustrate a cup-like overall structure forming a hollow suction recess of generally closed trough-like or cup-like shape, the ends of the ablation head need not be closed. Instead, the entire head may have the form of an open-ended channel (e.g., with the cross-section of FIG. 1C) that allows the ablation head to be more readily drawn along the tissue surface. Moreover, the ablation head may achieve the desired tissue-layer re-orientation or deformation simply by contact pressure without the use of a suction component.

In the implementation of the device as shown in FIG. 1A, the device has a handle 20 which is held by the surgeon, and the shaft 30 is preferably a flexible or malleable shaft that can be bent to allow the ablation head to be positioned at a desired location. This is particularly useful for accessing postero-lateral positions on the heart, in either open or endoscopic surgeries. The device is connected to an external source of vacuum to apply suction to the gripping apertures 48, and is connected to an RF generator assembly (not shown) to power the electrodes. Typical vacuum levels are between about minus 100 and about minus 500 mm of Hg. The preferred vacuum pressure is about minus 400 mm Hg. The vacuum and energy may be controlled through a suitable external control (e.g., a foot switch or valve) and/or it may be controlled through valve or switch control buttons 22a, 24a in the handle of the device as illustrated. Advantageously, the suction head locally clamps and immobilizes the tissue contacted by the ablation head.

In other or further embodiments a clamp can also be incorporated into the device to allow it to be clamped to a retractor and used as a heart stabilizer. In that case, the elongated body 30 may be implemented as a rigid shaft, or as an articulated shaft that may be rigidly locked once it is in position, so that the ablation head 40 then acts as a clamping foot to immobilize tissue. A separate clamping foot may alternatively be provided, such as a U-shaped suction foot or rigid clamp foot, that in use is positioned against the heart and locked to a retractor frame to immobilize a region of cardiac tissue that is to be ablated. The ablation head is then positioned to ablate a lesion on the still-beating heart. The ablation device may be manually held, or may itself attach to the retractor frame. Furthermore, in some embodiments, the suction passages 48 may be omitted, and the ablation head may position and immobilize cardiac tissue simply by being pressed against the tissue, forcing it into the groove or channel 44.

Figure 2A:
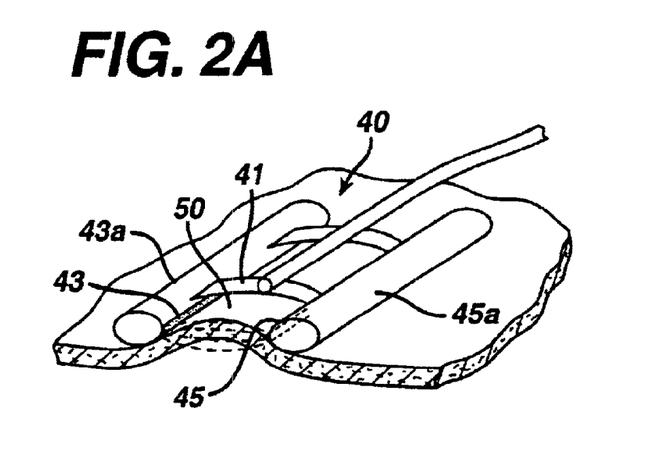
FIGS. 2A–2D illustrate details, respectively, of four further embodiments of the invention.

FIGS. 2A–2D schematically illustrate various suitable ablation head shapes and electrode configurations useful for devices of the present invention. As shown in FIG. 2A, one embodiment may be implemented with a particularly simple structure, such as two rods or bars 43a, 45a that are spaced parallel to each other (e.g., with cross braces 41) and have respective electrode faces 43, 45 facing each other across the gap therebetween. The bars press into cardiac tissue so that, as shown, the tissue deforms upward into the gap between electrodes to position its thickness dimension in the interelectrode paths. This embodiment need not (but may) possess a suction-gripping structure.

Figure 2B:
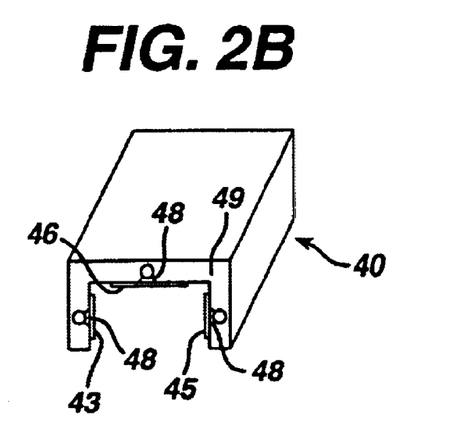

FIG. 2B shows another embodiment, in which the cavity or channel is substantially rectangular, and vacuum apertures 48 are positioned at sides and top of the channel 44. Insulating material 49 may form part of the overall structure, supporting and positioning the electrodes. Electrodes 43, 45 are positioned on opposed sides, and the electrode spacing is about twice the channel depth. The channel depth, in turn, is preferably comparable or about equal to the thickness of the target tissue layer. With this geometry, the cardiac wall is pulled into the channel and is bent, curved, or even folded, but the electrodes are still sufficiently closely spaced to provide low impedance deep ablation paths entirely through the tissue.

The term "bipolar" does not necessarily mean that only two electrodes are present. Rather, it is intended to indicate that each relevant group of ablation current paths extends locally between two electrodes carried by the device, rather than between one electrode and a general remote or external return electrode. Thus, the ablation head may technically be multipolar, with multiple pairs of electrodes defining different ablation path segments to span the tissue thickness at one or more positions. Thus, in FIG. 2B a third electrode 46 is shown on the bottom of the channel. In use, the two side electrodes 43, 45 may be attached to a common drive lead, and opposed to electrode 46. In that case, the paths from electrode 43 to 46, and from electrode 45 to 46, define two short sets of ablation path segments extending through tissue obliquely toward the center from the channel side walls. The tissue itself is deformed or bent by the ablation head, so that the effective current paths ablate through the thickness of the layer. In use, when the ablation head is activated, these paths form a relatively broad band of ablated tissue extending through the layer; when the tissue layer is thinner and conforms closely to the ablation head contour, the electrode structure may form two parallel ablated bands in the tissue.

Figure 2C:
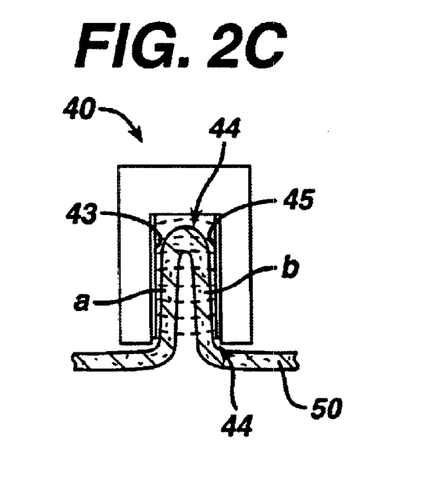
Figure 2D:
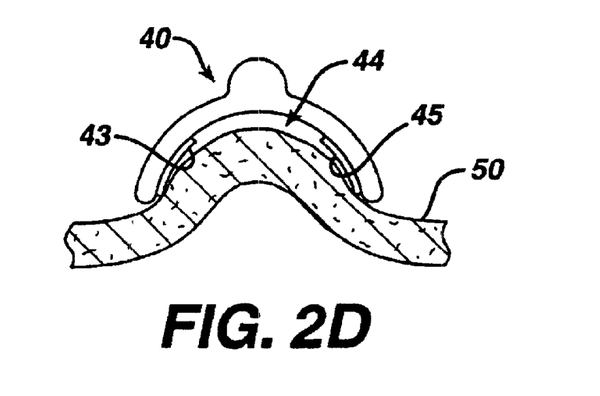

FIGS. 2C and 2D illustrate channel shapes in other embodiments of the invention. As shown in FIG. 2C, the channel 44 may be deep enough to fold the suction-gripped tissue, so that two distinct bands of tissue, denoted a and b are positioned across the high current inter-electrode current path. In this case, two transmural bands of ablated tissue are formed, and these are separated from and parallel to each other. In other embodiments, the channel 44 may simply be of a slightly concave shape as shown in FIG. 2D. In such case, the channel positions the electrodes 43, 45 apart obliquely with respect to the nominal tissue plane, simply bending the cardiac wall tissue upwardly between them sufficiently so that the interelectrode low impedance pathways have enhanced transverse components and span the tissue through its thickness dimension, creating a fully transmural ablation.

In any of the above configurations, the ablation head preferably has a tissue contacting surface (such as the peripheral surface 41 in FIG. 1B) that is soft or tissue-compliant. This contact area or active foot may be a malleable seal made from a material such as a polyurethane, polydimethylsiloxane (PDMS), or other soft elastomeric material, in order to provide a good seal to the irregularly shaped heart surface. The electrodes 43, 45, 46 contained in the head can be made from stainless steel, titanium or other non-corroding biocompatible conductive material. The malleable shaft or body 30 could also be made from the same materials, or may be constructed with suitable hybrid structure such as a polymer with embedded malleable metal cable. As noted above, the shaft or body 30 preferably also contains the electrode lead-in conductors, and the suction passage (when a suction gripper is provided) leading to the handle. The insulator material surrounding or supporting the electrodes can be rigid and made from polycarbonate, polymethylmethacrylate (PMMA) or other biocompatible polymer. Alternatively, it may be flexible or semi-flexible, and made, for example, from a polyurethane, polydimethylsiloxane (PDMS) or other elastomer. When the structure of the ablation head as a whole is made flexible or shapeable, the parallel electrodes may be bent by hand to better conform to a desired target and blocking lesion geometry.

The ablation devices of the present invention thus have a contact face that positions a tissue layer, illustratively the cardiac wall, such that two or more electrodes in bipolar arrangement on one side of the layer (illustratively, the epicardial or the endocardial surfaces of the heart) ablate tissue entirely through the layer. The channel operates to deform and orient the tissue layer and position electrodes so their higher current short paths span the layer thickness, and in various embodiments may pinch the layer to draw the distal tissue surface into the ablation paths. By bending the tissue in relation to the electrode structure, the distal reach of the ablation paths is better tailored to the tissue layer, and this avoids coagulating blood in the heart chamber (when ablation is performed epicardially) or damaging pericardial tissue (when performed endocardially).

Other embodiments of the invention may apply this tissue-positioning structure to both sides of the layer of tissue. That is, the device may press against the tissue from opposite sides, and deform or position the tissue with its thickness across current paths of electrodes on each side.

Figure 5A:
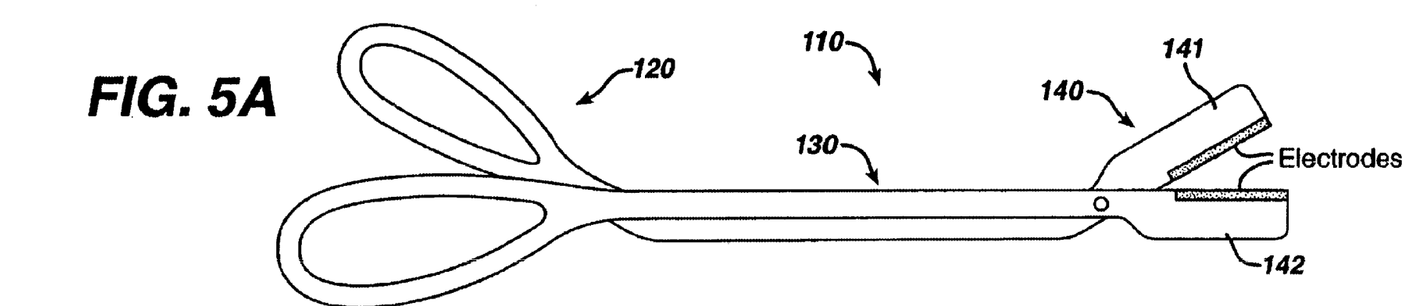
FIGS. 5A–5E illustrate another embodiment of the invention and its use for ablating tissue.
Figure 5B:
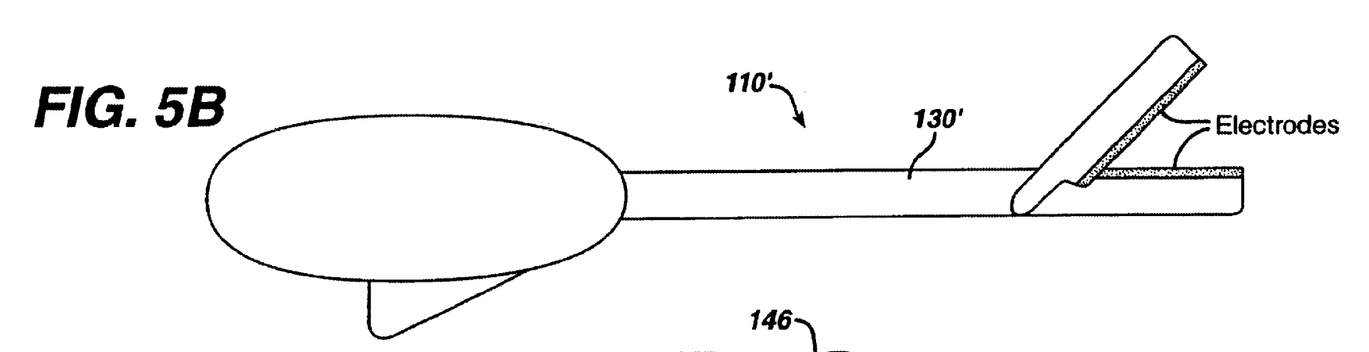
Figure 5C:
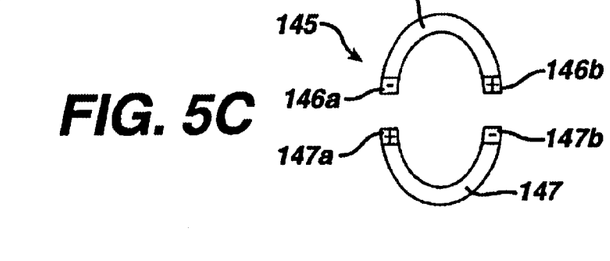

FIG. 5A illustrates a side view of one such device 110, having a scissors-like handle 120 and an elongated body 130 extending to a distal ablation head 140 that includes opposed ablation jaws 141, 142. The device may be configured with internal rods or cables such that the jaws 141, 142 are opened and closed by the handle 120 without movement of the body 130. Alternatively, for use in an open surgery, the body may comprise two arms, and actuation may employ a forceps-like articulation. FIG. 5B illustrates another two-jaw embodiment 110', having a tubular body 130' interconnecting the handle and the jaws. Control buttons or electrode/vacuum lines are omitted for clarity. FIG. 5C shows an end view of one electrode structure 145 useful in the embodiments of FIGS. 5A and 5B. As shown, the structure 145 includes a first jaw 146 having ablation electrodes 146a, 146b for contacting tissue on a first side, and a second jaw 147 having ablation electrodes 147a, 147b for contacting tissue on the opposite side when a tissue layer is gripped between the jaws. The illustrated electrodes are poled +/− on one jaw, and −/+ on the opposite jaw.

Figure 5D:
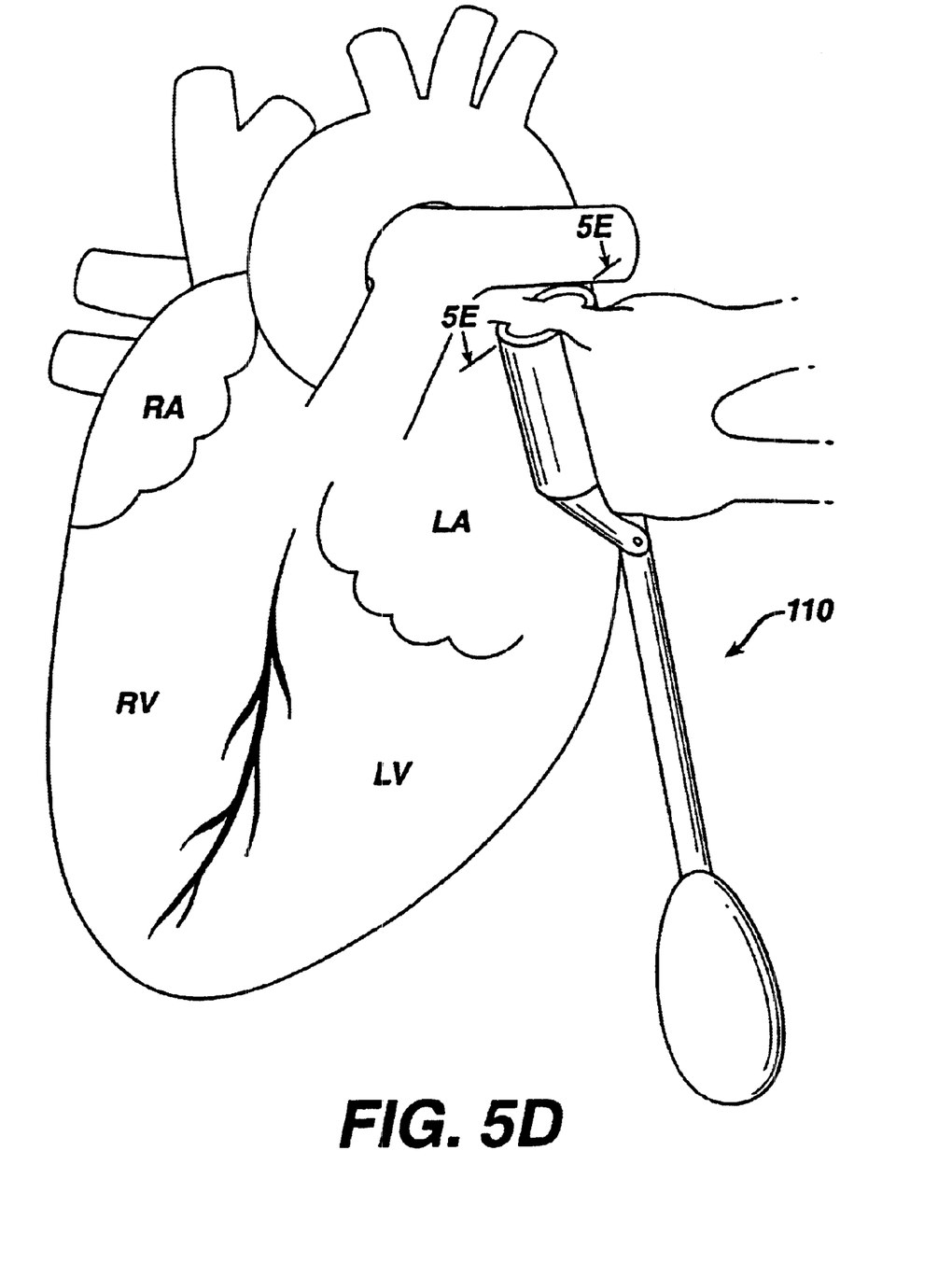
Figure 5E:
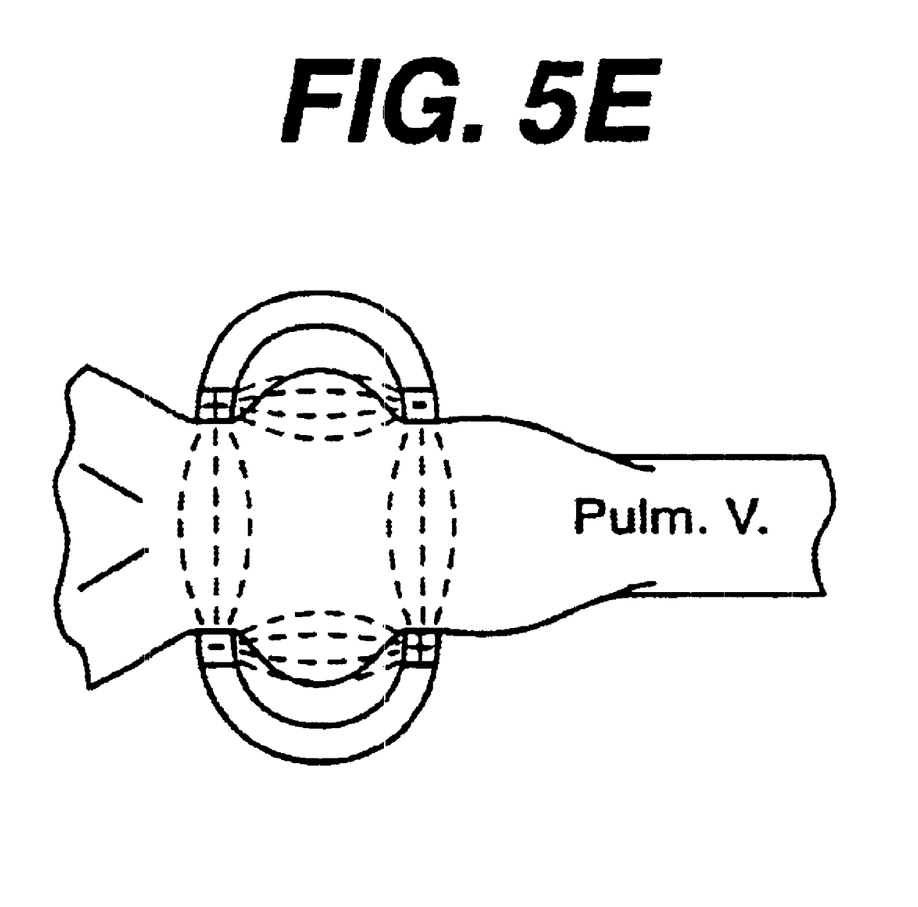

FIG. 5D illustrates the ablation device of FIG. 5B gripping the outside of the atrium about the junction of two pulmonary veins (illustratively a superior and an inferior vein on the left side). FIG. 5E is a cross-sectional view similar to FIG. 5C showing the atrial tissue, when gripped as in FIG. 5D, between the electrodes. The resulting current paths through the atrial wall for electrode pairs of the illustrated polarity, e.g., for the configuration where electrodes 146a, 147b are of like polarity. The current paths extend through the bent layer of tissue between electrodes of one jaw, and also through both layers between electrode of opposite jaws, forming well defined field lines and current paths for effecting fully transmural ablations.

Figure 4A:
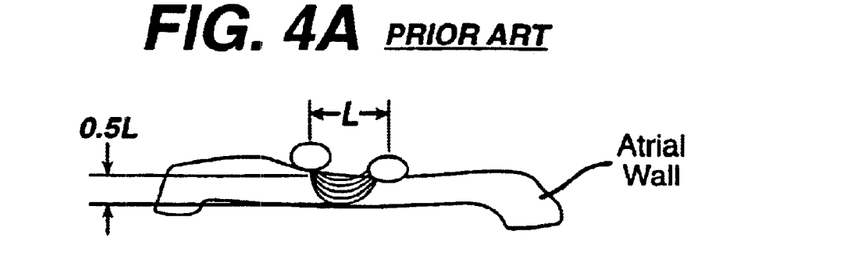
FIGS. 4A and 4B schematically illustrate RF ablation of the prior art, and of the present invention, respectively.

Various experiments have been conducted to assess the shape of lesion size versus electrode spacing and power for a conventional bipolar electrode configuration as shown in FIG. 4A. Lesions were created using two three-centimeter long electrodes, pressed against the right and left ventricle of an extracted bovine heart. RF energy was applied using a Pegasys bipolar generator. Table 1 illustrates the results.

TABLE 1

| Lesion # | Electrode Spacing | Power (W) | Duration (sec) | Extent at Surface (mm) | Depth of Lesion (mm) |
| --- | --- | --- | --- | --- | --- |
| 1 | 5 | 20 | 20 | 4 | 3 |
| 2 | 5 | 20 | 40 | 4.5 | 2.5 |
| 3 | 5 | 40 | 20 | 2.5 | 5 |
| 4 | 5 | 40 | 40 | 3 | 5 |
| 5 | 14 | 40 | 40 | 16 | 4 |
| 6 | 5 | 10 | 20 | 6 | 2 |
| 7 | 5 | 15 | 20 | 5 | 3 |
| 8 | 5 | 20 | 10 | 5 | 3 |
| 9 | 14 | 20 | 40 | 10 | 6 |
| 10 | 14 | 40 | 40 | 12 | 6 |

Figure 4B:
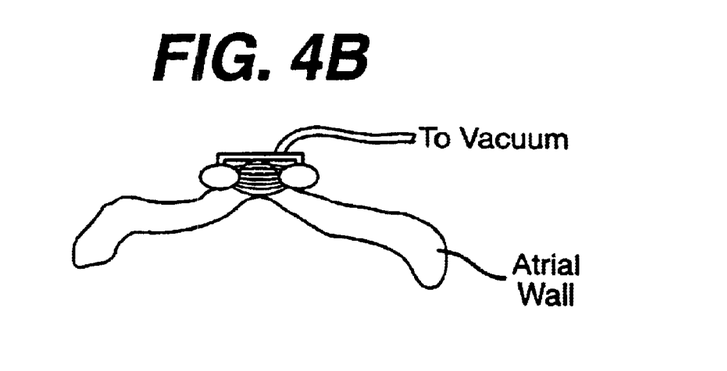

Tissue was ablated by applying two electrodes to the surface of the atrium, with the electrodes spaced a known distance apart and driven with an RF generator to produce an ablation lesion. The lesion depth is approximately half its surface extent, as shown in Table 1. Thus, a fully transmural lesion through the wall of a four millimeter thick atrium may be created using electrodes that are spaced roughly eight millimeters apart. However, the distal current paths in tissue are longer, of lower impedance and extend relatively tangentially to the tissue surface, exposing a large surface area of the chamber wall, so there is some risk of thrombogenesis in the interior. By using the electrode configuration of the present invention, as shown in FIG. 4B, with the tissue drawn up between the electrodes, the distal reach of the ablation energy is tailored to the tissue layer to more safely and effectively perform a fully transmural ablation. A preferred embodiment employs suction at one or more regions (center of channel, or center and sides) to draw the tissue in. However, as noted above, suitable tissue deformation or bending may also be achieved by pressing the electroded ablation head structure against the cardiac surface. Another embodiment (not illustrated) may have a mechanical forceps or clamping structure to actively pinch the target tissue area and position the tissue layer for fully transmural ablation without introducing ablation current into blood in the cardiac chamber.

The invention has particular utility for cardiac ablation, where the wall thickness may be large enough (e.g., four to eight millimeters) to impede safe or effective RF ablation when undertaken from a single side of the cardiac wall. As such, devices of the present invention may be employed to contact the outside of the heart and perform an epicardial ablation, or may be inserted into the heart and applied endocardially to a chamber wall. The enhanced contact and conduction paths of the invention make the ablation head especially useful to ablate lesions at the ostia of the left atrium, where tissue thickness and shape are subject to considerable variation and the posterior aspect is somewhat occluded or difficult to access. The handle allows flexibility in positioning the ablation head, and with the suction chuck to fasten in a defined position, the device maintains its position well, and may be used on a beating heart as well as a stopped heart. In either case, delivery may be effected by any of several approaches. Representative steps for several implementations of an ablation method of the invention will illustrate its range of applicability.

The methods of the invention may be applied in an open chest procedure performed on a beating heart. In this case, the patient is sedated and placed under anaesthesia, and a median sternotomy or thoracotomy is performed to gain access to the heart. The target area for creating lesions is determined on the epicardial surface, and epicardial fat is dissected away. The shaft is then bent to an appropriate shape to position the ablation head on the target site, the ablation head is contacted to the epicardial surface, and suction is applied to locally immobilize the heart wall at the area of contact. The ablation electrodes are then energized (e.g., for at least about 30 seconds at a 30 Watts power setting). The ablation head may then be re-positioned, secured by suction, and the electrodes activated one or more additional times until a full blocking lesion set has been created.

The methods of the invention may also be applied in an open chest procedure with the heart stopped, but still closed, and the ablation performed epicardially. In this case, the patient is sedated and placed under anaesthesia, and a median sternotomy or thoracotomy is performed to gain access to the heart. The heart is arrested and the major vessels connected to a heart-lung machine, placing the patient on cardiopulmonary bypass (CPB). The target area for creating lesions is determined on the epicardial surface, and epicardial fat is dissected away from the target region. The shaft of the ablation device is then bent to an appropriate shape to position the ablation head on the target site, the ablation head is contacted to the epicardial surface, and suction is applied to locally immobilize the heart wall at the area of contact. The ablation electrodes are then energized (e.g., for at least about 30 seconds at a 30 Watts power setting) to form a lesion at the immobilized site. The ablation head may then be re-positioned, secured by suction, and the electrodes activated again, with this sequence repeated one or more additional times until a full blocking lesion set has been created.

The methods may also be applied in connection with open heart surgery on a stopped heart. For example, during an open chest, mitral valve replacement operation, once the patient has been placed on CPB, the surgeon may open the left atrium, and determine the target sites on the endocardial surface where a lesion is to be made. Ablation then proceeds similarly to that described above for the epicardial surface, but is applied by contacting the ablation head to the endocardial surface in one or more sequences until the full lesion set has been created. The atrium is then closed. When used endocardially in this manner, an ablation tool of the invention may be configured with a handle and shaft that are primarily configured to push the ablation head against the endocardial surface, and the ablation head may be arranged to adjustably pivot to a desired angle across the axis of the shaft 30. Alternatively, the shaft may be bendable as described above to permit the ablation head to assume the necessary position and contact orientation.

Tools of the invention are particularly well adapted to endoscopic or to so-called minimally-invasive procedures performed on a beating heart. In this case, once the patient is sedated, the operation proceeds by introducing a trocar through the ribs to create a port for a thoracoscopic approach, and typically introducing a camera through a second such port for visualization. The ablation device is then introduced through the first port. The surgeon then determines the target area on the epicardial surface where a lesion is to be made, dissects away epicardial fat with suitable endoscopic tools, and proceeds endoscopically to carry out epicardial targeting and ablation steps substantially as described above for an open chest beating heart procedure. That is, the shaft is bent to a shape effective to position the active foot on the target site in the correct orientation. This may take one or more iterations as the tool is removed and reinserted to adjust the shape of the shaft, the ablation head is brought into contact with the target region on the heart wall, and suction is applied to locally immobilize the heart wall. The ablation electrodes are then energized to form a lesion at the immobilized site, and the ablation head is re-positioned, secured by suction, and the electrodes activated again. The repositioning/securing/electrode actuation sequence is repeated one or more additional times until a full blocking lesion set has been created.

Figure 3:
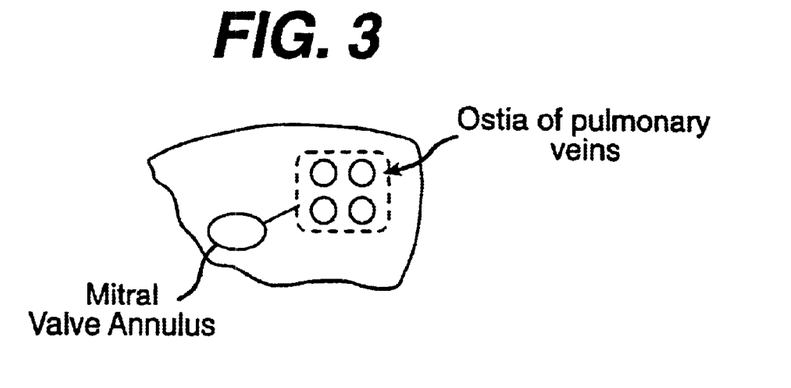
FIG. 3 illustrates a lesion pattern formed in accordance with the present invention.

The described ablation tools and methods of ablation are advantageously applied to form fully transmural myocardial lesions for blocking arrythmias originating at or propagating from a pulmonary vein. For this purpose, the ablation head may be formed with the electrodes shaped in short linear or arcuate segments, and the ablation head may be successively placed at positions to extend a lesion entirely around a pulmonary vein, or to place a blocking lesion circumscribing a pair of pulmonary veins. Similarly, the electrodes may be moved to create a different lesion shape. FIG. 3 schematically illustrates some suitable ablation paths, circumscribing plural pulmonary veins at the ostia and extending to the mitral valve. This lesion set isolates arythmogenic foci in the pulmonary veins and is effective against a common source of atrial fibrillation. Not only is the construction of the ablation head well adapted to fit in and around the posterior epicardial surface in region of the pulmonary veins, but the suction holding body assures that the myocardial tissue is fully transmurally ablated, despite the irregular and highly-varying wall thickness, and the rough or irregular surface features of the cardiac wall.

It will be appreciated that the invention provides an improved method and improved ablation devices for the practice of that invention. Those skilled in the art will appreciate that various modifications can be made to the described illustrative embodiments and techniques without departing from the scope of the present invention. The invention being thus disclosed, variations and modifications thereof will occur to those skilled in the art, and such variations and modifications are considered to be within the scope of the invention, as defined by the claims appended hereto and equivalents thereof. All documents, publications and references cited above are hereby expressly incorporated herein by reference in their entirety.

What is claimed is:

1. An ablation device comprising:
   a handle at a proximal end;
   an ablation head having a substantially planar tissue-contacting surface with a tissue-receiving cavity formed therein and having a plurality of electrodes disposed within the tissue-receiving cavity; and
   an elongated body interconnecting the handle and the ablation head;
   wherein the tissue-receiving cavity of the ablation head is shaped such that when the tissue-contacting surface of the ablation head is urged against a surface of a tissue layer, the tissue-receiving cavity receives tissue such that inter-electrode paths span a thickness dimension of the tissue to create a fully transmural ablation lesion.

2. The ablation device of claim 1, further comprising a suction assembly operative to grip tissue contacted to said ablation head.

3. The ablation device of claim 1, wherein the elongated body is deformable to set a shape for effectively positioning the ablation head at a desired site.

4. The ablation device of claim 1, wherein the plurality of electrodes extend along parallel paths.

5. The ablation device of claim 1, wherein the plurality of electrodes define a plurality of bipolar ablation path segments.

6. The ablation device of claim 1, wherein the plurality of electrodes are positioned and dimensioned to define oriented conduction paths positioned away from blood lying adjacent to the tissue layer.

7. The ablation device of claim 1, wherein the plurality of electrodes form a bipolar assembly with an electrode spacing of approximately ten millimeters across a channel of about five millimeters depth.

8. The ablation device of claim 1, wherein the ablation head forms a suction holder, connected through internal passages to a vacuum pressure of about 100–500 mmHg.

9. An ablation method comprising:
   providing an ablation head having a substantially planar tissue-contacting surface adapted to be disposed on a target tissue layer, the tissue-contacting surface including a tissue-receiving cavity formed therein with multiple electrodes disposed within the tissue-receiving cavity;
   placing the tissue-contacting surface of the ablation head into contact with a target tissue layer; and
   applying force to the ablation head such that the target tissue layer is forced into the cavity;
   whereby actuation of the electrodes in the ablation head is effective to ablate tissue along inter-electrode conduction paths forming a lesion extending entirely through the target tissue layer.

10. The ablation method of claim 9, further comprising the step of securing a surface of the target tissue layer to the ablation head.

11. The ablation method of claim 10, wherein the step of securing is performed by providing a suction passage in said ablation head to draw tissue thereagainst.

12. The ablation method of claim 9, wherein the target tissue layer is a myocardial wall, and actuating the multiple electrodes fully ablates a transmural lesion.

13. The ablation method of claim 9, wherein the step of placing the ablation head into contact with a target tissue layer is performed by contacting a cardiac surface.

14. The ablation method of claim 13, wherein the step of placing the ablation head into contact with a target tissue layer is performed to treat atrial fibrillation by contacting a circumferential region around a group of one or more pulmonary veins to create a conduction block.

15. The ablation method of claim 14, wherein the step of placing the ablation head into contact with a target tissue layer is performed by contacting endocardial tissue.

16. The ablation method of claim 14, wherein the step of placing the ablation head into contact with a target tissue layer is performed by contacting epicardial tissue.

17. The ablation method of claim 14, performed prophylactically after a CABG or similar surgical procedure.

18. The ablation method of claim 9, wherein the cavity has a depth about equal to said thickness dimension and defines an electrode spacing greater than approximately said thickness dimension.

19. The ablation method of claim 9, wherein the cavity has a shape selected from the group consisting of rectangular, circular, elliptical and a shallow dished concavity.

20. The ablation method of claim 9, wherein the cavity has a closed shape.

21. An ablation device comprising:

a handle at a proximal end;

an ablation head having a tissue-receiving cavity formed within a substantially planar tissue-contacting surface of the head, the cavity having a plurality of electrodes disposed therein; and an elongated body interconnecting the handle and the ablation head;

wherein the tissue-receiving cavity is shaped such that when urged against a surface of a tissue layer the cavity has a depth about equal to the thickness dimension of the tissue and defines an electrode spacing greater than approximately said thickness dimension.

22. An ablation method comprising:

providing an ablation head having a tissue-receiving cavity formed therein with ablation electrodes disposed therein;

placing the tissue-contacting surface of the ablation head into contact with a target tissue layer; and applying suction through the tissue-receiving cavity to draw tissue into the tissue-receiving cavity and position the tissue adjacent to the ablation electrodes;

whereby actuation of the ablation electrodes is effective to ablate tissue along inter-electrode conduction paths forming a lesion extending entirely through the tissue layer.

* * * * *